US 8,552,247 B2

(12) United States Patent
Noe et al.

(10) Patent No.: US 8,552,247 B2
(45) Date of Patent: Oct. 8, 2013

(54) AROMATICS RECOVERY BY EXTRACTIVE DISTILLATION

(75) Inventors: Robert J. L. Noe, Mount Prospect, IL (US); Bruce R. Beadle, Kildeer, IL (US); Lawrence E. Sullivan, Mount Prospect, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 13/428,731

(22) Filed: Mar. 23, 2012

(65) Prior Publication Data

US 2012/0247943 A1    Oct. 4, 2012

Related U.S. Application Data

(60) Provisional application No. 61/470,059, filed on Mar. 31, 2011.

(51) Int. Cl.
  *C10G 21/20*    (2006.01)
  *C07C 7/12*    (2006.01)

(52) U.S. Cl.
  USPC ........... 585/827; 585/829; 585/833; 585/860; 208/321; 208/326

(58) Field of Classification Search
  None
  See application file for complete search history.

(56) References Cited

U.S. PATENT DOCUMENTS

| | | | |
|---|---|---|---|
| 2,630,403 A | 3/1950 | Miller | |
| 2,964,465 A * | 12/1960 | Brown et al. | 208/314 |
| 3,089,250 A | 5/1963 | Victor | |
| 3,953,324 A * | 4/1976 | Deal et al. | 208/321 |
| 4,048,062 A | 9/1977 | Asselin | |
| 4,083,772 A | 4/1978 | Asselin | |
| 6,573,418 B2 | 6/2003 | Miller et al. | |
| 6,596,914 B2 | 7/2003 | Gore et al. | |
| 6,706,938 B2 | 3/2004 | Roeseler et al. | |
| 7,666,299 B2 | 2/2010 | Wu et al. | |
| 7,847,137 B2 | 12/2010 | Negiz et al. | |
| 7,871,514 B2 | 1/2011 | Lee | |
| 2010/0300939 A1 | 12/2010 | Noe et al. | |

FOREIGN PATENT DOCUMENTS

| EP | 964904 B1 | 7/2001 |
|---|---|---|
| EP | 1454976 A1 | 9/2004 |

OTHER PUBLICATIONS

Lee, "Two-Liquid-Phase Extractive Distillation for Aromatics Recovery", Ind. Eng. Chem. Res, 1987, vol. 26, No. 3, pp. 564-573.
Sircar, "Liquid-Phase Sorption-Enhanced Reaction Process", AlChe Journal, Nov. 1999, vol. 45, No. 11, pp. 2326-2332.
Eldridge, "Olefin/Paraffin Separation Technology: A Review", Ind. Eng. Chem. Res., 1993, vol. 32, No. 10, pp. 2208-2212.

* cited by examiner

*Primary Examiner* — Tam M Nguyen
(74) *Attorney, Agent, or Firm* — Mark R Willis

(57) ABSTRACT

The present invention relates to a process for recovering polar hydrocarbons from non-polar hydrocarbons, such as aromatics from non-aromatics, naphthenes from paraffins and isoparaffins, or olefins from paraffins and isoparaffins, in feed mixtures containing at least a measurable amount of heavier hydrocarbons. According to the invention, an improved extractive distillation (extractive-distillation) process is disclosed for recovering aromatic hydrocarbons including benzene, toluene, and xylenes from heavy ($C_9$+) hydrocarbons. The invention also relates to an improved extractive-distillation process for recovering mainly benzene and toluene from the $C_6$-$C_7$ petroleum streams containing at least a measurable amount of $C_8$+ hydrocarbons. This invention is further directed toward the regeneration and recovery of the extractive-distillation solvent utilized to recover and purify the aromatic hydrocarbons from the petroleum stream containing at least a measurable amount of hydrocarbons heavier than the intended product.

13 Claims, 1 Drawing Sheet

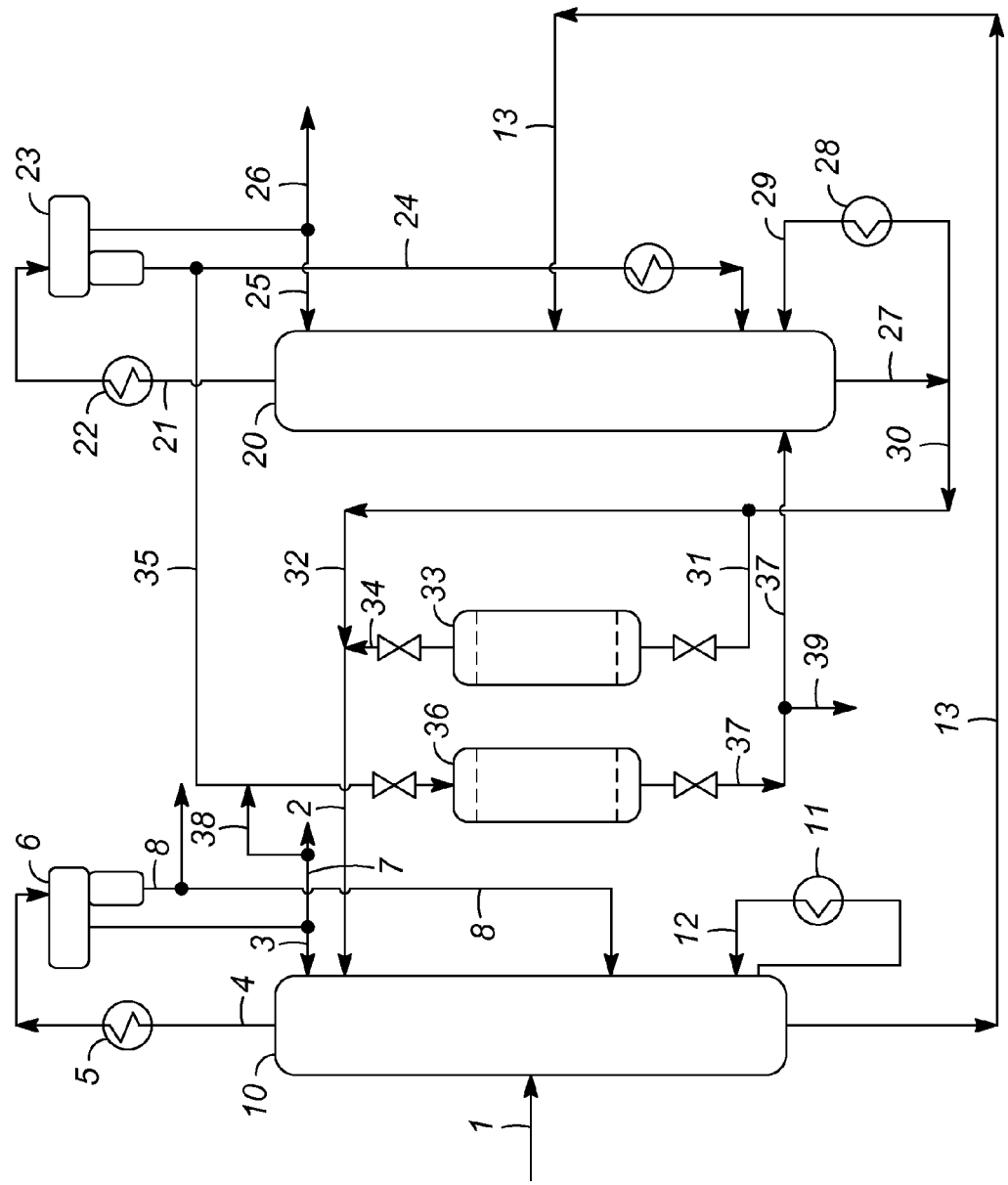

AROMATICS RECOVERY BY EXTRACTIVE DISTILLATION

CROSS-REFERENCE TO RELATED APPLICATION

This application claims the benefit of U.S. Provisional Application No. 61/470,059 filed on Mar. 31, 2011.

FIELD OF THE INVENTION

The present invention relates to the recovery of aromatic hydrocarbons from a stream containing a mixture of aromatic and aliphatic hydrocarbons. More specifically, the invention relates to an extractive distillation process for the recovery of aromatics and a method for purifying the extractive-distillation solvent for use in a closed solvent loop.

BACKGROUND OF THE INVENTION

Extractive distillation is a key separation method used in chemical processing, especially for the recovery of aromatics from hydrocarbon mixtures. A key aspect of extractive distillation is that a separating agent, a solvent with a high boiling point, is added to a component mixture for separation which increases relative volatility when the components have similar or close boiling points.

Aromatic hydrocarbons can be recovered from mixtures containing aromatic and non-aromatic hydrocarbons by liquid-liquid extraction. Examples of suitable feedstocks for extraction are mixtures containing benzene, toluene and xylene derived from the catalytic reforming of naphtha or from the hydrogenation of raw pyrolysis gasoline byproduct from olefin production.

Extractive distillation is an alternative aromatics-recovery process which typically is applied to lighter hydrocarbon fractions and comprises an extractive-distillation column and a solvent-recovery column. A nonvolatile solvent passes to an upper section and the hydrocarbon fraction is introduced to a middle section of the extractive-distillation column. As the solvent descends through the column, it preferentially extracts the polar components (aromatics) to form a rich solvent while the non-polar component vapor comprising non-polar components ascends to the top of the column. Overhead vapor is condensed, with a portion of the condensate being recycled to the top section of the extractive-distillation column as reflux while a net portion is withdrawn as a raffinate product. The rich solvent from the bottom of the extractive-distillation column, comprising the solvent and the polar components, is fed into a solvent recovery column to recover aromatics as an overhead product along with reflux to the recovery column. Bottoms from the solvent-recovery column are lean solvent, free of the feed components, which is recycled to the upper portion of the extractive-distillation column as the extractive solvent.

Extractive distillation requires less equipment, for example two instead of four separation columns, and has a lower energy requirement than solvent extraction, but the application of this process is restricted by requiring a narrower feedstock boiling range than liquid-liquid extraction. The feedstock to extractive distillation normally is obtained by fractionation of a wider-range hydrocarbon fraction. Extractive distillation most often is targeted to the recovery of benzene from a fraction rich in $C_6$ and $C_7$ hydrocarbons, but small amounts of heavy hydrocarbons remain even in such light fractions. These heavy hydrocarbons tend to remain with the rich solvent at the bottom of the extractive-distillation column due to their high boiling points, and accumulate in the solvent due to the solvent being circulated within a closed loop, with consequent inefficient column and process operation. These generally can only be removed from the solvent by increasing the temperature, vacuum level, and stripping steam of the solvent-recovery column, but this method is costly and may result in degradation of the solvent. There is a need for an efficient process to remove heavy hydrocarbons and products of degradation from the circulating solvent to reduce sludge and plugging in the system.

Solvent purification in a liquid-liquid extraction process is disclosed in U.S. Pat. No. 4,048,062 to G. Asselin, in which a portion of lean solvent is introduced into a solvent regeneration zone and stripped with steam to remove deteriorated solvent and impurities. Extractive distillation is widely referenced in patent and other literature. The process is generally described in F. Lee, et al., "Two Liquid-Phase Extractive Distillation for Aromatics Recovery", Ind. Eng. Chem. Res. (26) No. 3, 564-573, 1987. U.S. Patent Applications 2009/0038991 and 2010/0300939 disclose extractive distillation processes in which the solvent is subjected to washing and recovery to separate heavy hydrocarbons and sludge and avoid accumulation of hydrocarbons heavier than the desired product; relevant provisions of these applications are incorporated herein by reference thereto.

SUMMARY OF THE INVENTION

A broad aspect of the present invention is a method for recovering a substantially hydrocarbon-free, water-soluble polar-hydrocarbon-selective solvent from a solvent-rich stream comprising hydrocarbons and heavy waste products, the method comprising (a) introducing a hydrocarbon feedstock comprising polar and non-polar hydrocarbons into an intermediate section of an extractive-distillation column, introducing a circulating polar solvent into an upper section of the column, recovering a raffinate product comprising non-polar hydrocarbons and water overhead from the column, and removing a rich solvent comprising polar solvent and polar hydrocarbons from the bottom of the column; (b) introducing the rich solvent into a rich-solvent fractionator, recovering an extract product comprising polar hydrocarbons overhead from the fractionator and a contaminated solvent from the bottom of the column; (c) dividing the contaminated solvent into a first portion and a second portion and directing the first portion to a first solvent-purification vessel containing a solid adsorbent to yield a purified solvent and a contaminated adsorbent; (d) passing a portion of the raffinate product to a second solvent-purification vessel containing contaminated adsorbent to yield purified solid adsorbent and contaminated raffinate; (e) subjecting the first solvent-purification vessel of step (c) containing contaminated adsorbent to the method of step (d) and the second solvent-purification vessel of step (d) to the method of step (c); and (f) combining the second portion of contaminated solvent and purified solvent to provide the circulating polar solvent.

A more specific aspect of the invention is a method for recovering a substantially hydrocarbon-free, water-soluble polar-hydrocarbon-selective solvent from a solvent-rich stream comprising hydrocarbons and heavy waste products, the method comprising (a) introducing a hydrocarbon feedstock comprising aromatic and non-aromatic hydrocarbons into an intermediate section of an extractive-distillation column, introducing a circulating polar solvent into an upper section of the column, recovering a raffinate product comprising non-aromatic hydrocarbons and water overhead from the column, and removing a rich solvent comprising polar solvent and aromatic hydrocarbons from the bottom of the column; (b) introducing the rich solvent into a rich-solvent fractionator, recovering an extract product comprising aromatic hydrocarbons overhead from the fractionator and a contaminated solvent from the bottom of the column; (c) dividing the contaminated solvent into a first portion and a second portion and directing the first portion to a first solvent-purification vessel containing a solid adsorbent to yield a purified solvent and a contaminated adsorbent; (d) passing a portion of the raffinate product to a second solvent-purification vessel containing contaminated adsorbent to yield purified solid adsorbent and contaminated raffinate; (e) subjecting the first solvent-purification vessel of step (c) containing contaminated adsorbent to the method of step (d) and the second solvent-purification vessel of step (d) to the method of step (c); and combining the second portion of contaminated solvent and purified solvent to provide the circulating polar solvent.

A yet more specific aspect of the invention is a method for recovering a substantially hydrocarbon-free, water-soluble polar-hydrocarbon-selective solvent from a solvent-rich stream comprising hydrocarbons and heavy waste products, the method comprising (a) introducing a hydrocarbon feedstock comprising benzene and non-aromatic hydrocarbons into an intermediate section of an extractive-distillation column, introducing a circulating polar solvent into an upper section of the column, recovering a raffinate product comprising non-aromatic hydrocarbons and water overhead from the column, and removing a rich solvent comprising polar solvent and benzene from the bottom of the column; (b) introducing the rich solvent into a rich-solvent fractionator, recovering an extract product comprising benzene overhead from the fractionator and a contaminated solvent from the bottom of the column; (c) dividing the contaminated solvent into a first portion and a second portion and directing the first portion to a first solvent-purification vessel containing a solid adsorbent to yield a purified solvent and a contaminated adsorbent; (d) passing a portion of the raffinate product to a second solvent-purification vessel containing contaminated adsorbent to yield purified solid adsorbent and contaminated raffinate; (e) subjecting the first solvent-purification vessel of step (c) containing contaminated adsorbent to the method of step (d) and the second solvent-purification vessel of step (d) to the method of step (c); and, (f) combining the second portion of contaminated solvent and purified solvent to provide the circulating polar solvent.

BRIEF DESCRIPTION OF THE DRAWING

The FIGURE is a schematic illustration of an extractive-distillation process incorporating the solvent-purification step of the invention.

DETAILED DESCRIPTION OF THE INVENTION

This invention provides an improved extractive-distillation process for recovering polar hydrocarbons from non-polar hydrocarbons, such as aromatics from non-aromatics, naphthenes from paraffins and isoparaffins, or olefins from paraffins and isoparaffins, in feed mixtures containing at least a measurable amount of heavier hydrocarbons which are extracted from petroleum streams. In one of its specific applications, this invention relates to an improved extractive-distillation process for recovering aromatic hydrocarbons including benzene, toluene, and xylenes (BTX aromatics) from the $C_6$-$C_8$ petroleum streams containing at least a measurable amount of $C_9$+ hydrocarbons. In another specific application, this invention relates to an improved extractive-distillation process for recovering mainly benzene and toluene from the $C_6$-$C_7$ petroleum streams containing at least a measurable amount of $C_8$+ hydrocarbons.

More specifically, this invention is directed toward the regeneration, recovery and purification of the extractive-distillation solvent utilized to recover pure aromatic hydrocarbons from the hydrocarbon stream containing at least a measurable amount of hydrocarbons heavier than intend feedstock.

In a broad embodiment, a feed containing polar and non-polar hydrocarbons is introduced into a middle portion of an extractive-distillation column and a solvent-rich stream is fed into an upper portion of the extractive-distillation column as the selective solvent feed. A water-containing non-polar-hydrocarbon-rich stream is recovered from the upper portion of the extractive-distillation column. A first solvent-rich stream containing the aqueous solvent and the polar hydrocarbons is recovered from a bottom portion of the extractive-distillation column. The first solvent-rich stream is introduced into a middle portion of a solvent-recovery column and a polar hydrocarbon-rich stream, substantially free from said aqueous solvent and said non-polar hydrocarbons is recovered from an upper portion of the solvent-recovery column. A second solvent-rich stream is removed from a bottom portion of the solvent-recovery column and a greater portion of the second solvent-rich stream is fed into the upper portion of the extractive-distillation column. A lesser fraction of the second solvent-rich stream is passed into a first solvent-purification vessel containing an adsorbent suitable for removing hydrocarbons and other contaminants from the solvent, and purified solvent from this vessel is combined with the greater portion of the solvent-rich stream to the upper portion of the extractive-distillation column. A portion of the raffinate product is sent to a second solvent-purification vessel containing adsorbent contaminated by hydrocarbons and other contaminants and removes the contaminants, joining the raffinate product as feed to the solvent-regeneration column. Water and any hydrocarbons and other compounds having boiling points lower than or equal to that of said aqueous solvent is recovered from the upper portion of the solvent regeneration zone.

Although the techniques are applicable to a multitude of hydrocarbon mixtures, the discussion of the FIGURE will be directed primarily to the separation and recovery of aromatic hydrocarbons from a mixture with non-aromatics, including paraffins, isoparaffins, naphthenes, and/or olefins. A hydrocarbon feed containing a mixture of aromatic and non-aromatic hydrocarbons is fed via conduit 1 to a middle section of an extractive-distillation column 10, while a lean solvent is fed via conduit 2 to near the top of the extractive-distillation column below the entry point of overhead reflux 3. Non-aromatics vapor exiting the top of the extractive-distillation column through conduit 4 is condensed via condenser 5 and transferred to an overhead receiver 6, which serves to effect a phase separation between the non-aromatic raffinate and the water phase. A first portion of the non-aromatic raffinate is recycled to a top section of the extractive-distillation column as reflux via conduit 3, while a second portion of the non-aromatic raffinate is withdrawn as a raffinate product through conduit 7. The water phase in conduit 8 is returned to the extractive distillation column 10.

The rich solvent stream containing the solvent, aromatic hydrocarbons, and measurable heavy hydrocarbons is withdrawn from the bottom section of the extractive-distillation column and heated in a reboiler 11 and recycled to the bottom section of the extractive-distillation column via conduit 12 to generate vapor to the column. The rich solvent from the bottom of the extractive distillation column 10 is fed to a middle section of the solvent-recovery column 20 through conduit 13.

An aromatic concentrate containing water and being substantially free of solvent and non-aromatic hydrocarbons, is withdrawn from solvent-recovery column 20 through conduit 21 as an overhead vapor stream, condensed in condenser 22, and introduced into an overhead receiver 23. The overhead receiver serves to effect a phase separation between the aromatic-hydrocarbon phase and the water phase 24. A first portion of the aromatic hydrocarbon phase is recycled to a top section of the solvent-recovery column as the reflux via conduit 25, while a second portion of the aromatic hydrocarbon phase is withdrawn as the aromatic hydrocarbon product through conduit 26. The water phase is transferred through conduit 24 preferably to a steam generator to form stripping steam for the solvent-recovery column. In order to minimize the bottom temperature of the solvent-recovery column, the overhead receiver 23 is connected to a vacuum source to generate sub-atmospheric condition in the solvent-recovery column.

A contaminated lean solvent stream containing a measurable amount of heavy hydrocarbons, including aromatics heavier than the product and decomposed materials, is withdrawn from a bottom portion of the solvent-recovery column through conduit 27. Small amounts of olefinic hydrocarbons are more concentrated in the heavy hydrocarbons fraction, and the load of a clay tower in an aromatics complex for olefinic hydrocarbons removal from the aromatic product can be significantly reduced by keeping the heavy hydrocarbons at the bottom of the solvent-recovery column with the lean solvent; the olefinic as well as heavy aromatic hydrocarbons can be removed from the closed solvent loop by the purification step of this invention. A portion of the lean solvent in conduit 27 is heated in a reboiler 28 and recycled to the bottom section of the solvent-recovery column via conduit 29 to generate vapor to the column, while the remaining portion of the contaminated lean solvent in conduit 30 passes to the solvent-purification section.

The solvent-purification section comprises two or more vessels which are alternatively in adsorption and regeneration mode. Part of the lean solvent may bypass the solvent-purification section as lean solvent to extractive distillation in conduit 2. A first portion of contaminated solvent to be purified is directed via conduit 31 to one or more first solvent-purification vessels in vessel 33 containing a solid adsorbent, which adsorbs contaminants from the solvent to yield a purified solvent in conduit 34 and a contaminated adsorbent in vessel 33. A second portion of contaminated solvent in conduit 32 is combined with purified solvent to provide a circulating solvent to extractive distillation in conduit 2. A portion of the water phase in conduit 24 is sent via conduit 35 to one or more vessels 36 which have received contaminated solvent and contain contaminated adsorbent to yield contaminated solid adsorbent essentially free of solvent in vessel 36 and water and solvent in conduit 37. A portion of the raffinate of stream 7 is used to remove the heavy contaminant from the adsorbent in stream 38 and remove contaminant from the process in conduit 39

The water-soluble, aqueous solvent is selected from the list comprising sulfolane, alkyl-sulfolane, N-formyl morpholine, N-methyl pyrrolidone, tetraethylene glycol, triethylene glycol, diethylene glycol, and mixtures thereof. In one aspect, the water-soluble solvent is aqueous sulfolane, in another aspect, the water-soluble solvent is aqueous N-formyl morpholine, in an alternate aspect, the water-soluble solvent is aqueous N-methylpyrrolidone, and in yet another aspect, the water-soluble solvent is aqueous tetraethylene glycol. Preferably, the solvent consists essentially of sulfolane.

Degradation of the sulfolane solvent occurs at temperatures above 200° C. in an inert atmosphere and increases significantly in oxygen-containing atmosphere, where air leaks through the extractive-distillation process equipment which operates in a vacuum. The primary products from degradation of sulfolane are sulfur dioxide and oxygen-containing organic compounds, such as aldehydes, organosulfonic acids, carboxylic acids, etc., which are removed from the solvent using the process of the invention.

A variety of adsorbents are suitable for contaminant removal in the solvent-purification vessels. Polymeric adsorbents such as those used for oil recovery are suitable adsorbents. Other suitable sorbents include alumina, silica, silica-alumina, zeolitic and non-zeolitic molecular sieves and activated carbon.

The purified organic solvent fluid flowing through the fluid flow pathway may be re-circulated such that it undergoes multiple passes through the solvent-purification vessels. The purification zone typically is operated at a temperature of 0° to 100° C. and a pressure of 1 to 100 atmospheres.

The above description and examples are intended to be illustrative of the invention without limiting its scope. The skilled routineer will readily understand how to extrapolate parameters of the disclosure to other embodiments of the invention. The invention is limited only by the claims set forth herein.

The invention claimed is:

1. A method for recovering a substantially hydrocarbon-free, water-soluble polar-hydrocarbon-selective solvent from a solvent-rich stream comprising hydrocarbons and heavy waste products, the method comprising:
   (a) Introducing a hydrocarbon feedstock comprising polar and non-polar hydrocarbons into an intermediate section of an extractive-distillation column, introducing a circulating polar solvent into an upper section of the column, recovering a raffinate product comprising non-polar hydrocarbons and water overhead from the column, and removing a rich solvent comprising polar solvent and polar hydrocarbons from the bottom of the column;
   (b) introducing the rich solvent into a rich-solvent fractionator, recovering an extract product comprising polar hydrocarbons overhead from the fractionator and a contaminated solvent from the bottom of the column;
   (c) dividing the contaminated solvent into a first portion and a second portion and directing the first portion to a first solvent-purification vessel containing a solid adsorbent to yield a purified solvent and a contaminated adsorbent;
   (d) passing a portion of the raffinate product to a second solvent-purification vessel containing contaminated adsorbent to yield purified solid adsorbent and contaminated raffinate;
   (e) subjecting the first solvent-purification vessel of step (c) containing contaminated adsorbent to the method of step (d) and the second solvent-purification vessel of step (d) to the method of step (c); and,
   (f) combining the second portion of contaminated solvent and purified solvent to provide the circulating polar solvent.

2. The method according to claim 1 wherein said polar hydrocarbons are aromatic and said non-polar hydrocarbons are paraffinic, naphthenic, and olefinic.

3. The method according to claim 1 wherein the water-soluble, aqueous solvent is selected from the group comprising sulfolane, alkyl-sulfolane, N-formyl morpholine, N-methylpyrrolidone, tetraethylene glycol, triethylene glycol, diethylene glycol, and mixtures thereof.

4. The method according to claim 3 wherein said water-soluble solvent is aqueous sulfolane.

5. The method according to claim 3 wherein said water-soluble solvent is aqueous N-formyl morpholine.

6. The method according to claim 3 wherein said water-soluble solvent is aqueous N-methylpyrrolidone.

7. The method according to claim 3 wherein said water-soluble solvent is aqueous tetraethylene glycol.

8. The method according to claim 1 wherein the adsorbent is selected from the group comprising alumina, silica-alumina, clay, a zeolitic molecular sieve and an ion-exchange resin.

9. The method according to claim 1 wherein the extractive-distillation column is operated under such conditions to maximize the benzene recovery in said first solvent-rich stream by keeping substantially all C9+hydrocarbons in said first solvent-rich stream.

10. The method according to claim 1 wherein said solvent-recovery column is operated under such conditions to strip only C8 and lighter hydrocarbons from said first solvent-rich stream and to keep substantially all C9 and heavier hydrocarbons in said second solvent-rich stream.

11. The method of claim 1 further comprising passing a water stream through the contaminated adsorbent of step (c) to remove solvent.

12. The method of claim 1
wherein said polar hydrocarbons comprise aromatic hydrocarbons and said non-polar hydrocarbons comprise non-aromatic hydrocarbons.

13. The method of claim 1
wherein said polar hydrocarbons comprise benzene and said non-polar hydrocarbons comprise non-aromatic hydrocarbons.

* * * * *